United States Patent

Knapik et al.

[11] Patent Number: 5,967,145
[45] Date of Patent: Oct. 19, 1999

[54] HARNESS FOR LONG-TERM STRETCHER CARRY

[75] Inventors: Joseph J. Knapik, Edgewood, Md.; Valerie J. B. Rice, Houston, Tex.; Dennis M. Hash, Aberdeen; William H. Harper, Bel Air, both of Md.

[73] Assignee: The United States of America as represented by the Secretary of the Army, Washington, D.C.

[21] Appl. No.: 09/072,550

[22] Filed: May 5, 1998

[51] Int. Cl.$^6$ .................................................. A61B 19/00
[52] U.S. Cl. .......................... 128/869; 128/874; 128/875
[58] Field of Search .................. 128/846, 869, 128/873–876; 297/484, 485

[56] References Cited

U.S. PATENT DOCUMENTS

| | | | |
|---|---|---|---|
| 1,123,278 | 1/1915 | Hallett | 128/874 |
| 5,031,639 | 7/1991 | Wolfer | 128/874 |
| 5,163,450 | 11/1992 | Cadichon | 128/874 |

OTHER PUBLICATIONS

Cardiovascular Responses to Holding and Carrying Weights by Hand and By Shoulder Harness, Lind, AR.R and McNicol, G.W. Journal of Applied Physiology, vol. 25, No. 3, Sep. 1968, pp. 261–267.

A Usability Assessment of Two Harnesses for Stretcher–Carrying, Rice, et al, Advances in Industrial Ergonomics and Safety IV< Edited by S. Kumar, Taylor & Francis, 1992, pp. 1269–1274.

The Effects of Gender, International Journal of Industrial Ergonomics, 18 (1996), pp. 27–49 Lind and McNicol.

*Primary Examiner*—Michael A. Brown
*Attorney, Agent, or Firm*—Paul S. Clohan, Jr.; Mark D. Kelly

[57] ABSTRACT

A harness for wearing by a person allows the weight of a stretcher with a casualty to be carried on the shoulders, hips, or hands of the person. The harness has two padded shoulder straps which are vertically adjustable. The shoulder straps are connected by a horizontal piece of fabric which is horizontally adjustable, bringing the shoulder straps closer together or farther apart. The shoulder straps are attached to a padded hip belt. The hip belt is horizontally adjustable and has four fabric loops, two on each side. The loops are used for the stretcher arms. The two arms of a stretcher are placed in the loops, one arm in two loops. The weight of the stretcher is thus carried on the loops and the harness allows the weight of the stretcher to be transferred to the shoulders, hips, or hands.

11 Claims, 2 Drawing Sheets

HARNESS FOR LONG-TERM STRETCHER CARRY

BACKGROUND OF THE INVENTION

The invention relates in general to harnesses for carrying stretchers, and in particular to a harness that is capable of shifting the load to different portions of the carrier's body.

Stretchers for injured, sick, or otherwise incapacitated individuals are currently carried in the hands. Two or four people usually carry the stretcher. If two people carry the stretcher, both individuals use both hands and each carrier must bear ½ of the load. If four people carry the stretcher, each use only one hand and each person bears ¼ of the total load. Carriage times are very short because the carriers must rest often, or other people must assist in the carriage. When carrying by hand, the carriers are using the small muscle groups of the hands and arms which fatigue rapidly.

There have been two groups in the medical and ergonomic literature who have attempted to improve stretcher carriage in the past. The first group was Lind and McNicol (See Lind, A. R. and McNicol, G. W., "Cardiovascular Responses to Holding and Carrying Weights By Hand and By Shoulder Harness", Journal of Applied Physiology, Volume 25, Number 3, Sep. 1968, United States, pp 261–267) who demonstrated that time to fatigue could be considerably extended when using a shoulder harness to carry a litter as opposed to hand carriage. During hand carriage, blood pressure and heart rate rose progressively until fatigue ensued in an average of about 3 minutes. With the shoulder harness, only small changes in cardiovascular measures were noted and individuals were often able to continue for the 15 minute limit of the study. Lind and McNicol did not provide a description of the type of harness used.

The second group was Rice et al (See V. Rice, "A Usability Assessment of Two Harnesses for Stretcher-Carrying," Advances in Industrial Ergonomics and Safety IV, Edited by S. Kumar, Taylor & Francis, 1992, pp 1269–1274; V. Rice, M. Sharp, W. Tharion, T. Williamson, "The Effects of Gender, Team Size, and a Shoulder Harness on a Stretcher-Carry Task and Post-Carry Performance," International Journal of Industrial Ergonomics, 18 (1996) pp 27–49) who confirmed and extended the findings of Lind and McNicol. Longer times to fatigue were achieved when men and women carried a weighted manikin (about 80 kg) using two specially designed and well described litters. Carriage times were 23 minutes with the harness and six minutes with hand carriage; however, carriage times were limited to 30 minutes so "true" times to exhaustion were not obtained. The harness used by Rice et al was designed to move the load from the hands and arms to the shoulders. The carrier's subjective reports of pain, soreness, and discomfort (PSD) suggest this was successfull: with hand carriage subjects reported more PSI) in the hands and forearm, while with the shoulder harness more PSD was reported in the neck, shoulders, chest, upper back, thighs and calves.

The present invention improves on the shoulder harness described by Rice et al. One improvement is a well padded hip belt. The hip belt allows transferring of the load from the shoulders to the hips. Proper tightening of the hip belt places the load on the top of the hips and vertical displacement allows the load to be carried on the lower body. The lower body contains most of the muscle mass in the body so that the load is distributed over a large amount of muscle tissue compared to carriage by the hands or a shoulder harness alone.

Another improvement is providing for load shifting. This is accomplished by providing the carrier with easy to reach adjustments (buckles, clips, straps and the like) which allow the carrier to transfer the load to different body parts at different times. When the hip belt is tightened and shoulder straps loosened, the load is placed on the hips. By loosening the hip belt and tightening the shoulder straps the load can be placed on the shoulders. By pulling on the horizontal shoulder strap connector the load can be shifted to different parts of the shoulders. The load can also be carried in the hands since the carrier can reach down between the two loops on either side and grasp the handles of the stretcher. Load shift should improve load carriage time because a formerly loaded muscle group can now rest and thus replenish energy and allow a return of blood flow to muscular and cutaneous areas which had previously experienced pressure.

SUMMARY OF THE INVENTION

It is an object of the present invention to provide a device which allows the weight of a stretcher with a casualty to be carried on the shoulders, hips, or hands.

This and other objects of the invention are achieved by a harness for wearing by a person carrying a stretcher, comprising a padded hip belt; a pair of padded shoulder straps joined together at a portion on a rear of the harness; first and second pairs of shoulder strap adjustment devices disposed on a front and the rear of the harness, respectively, for connecting the pair of shoulder straps to the hip belt, lengths of the first and second pairs of shoulder strap adjustment devices being adjustable; a hip belt adjustment device having an adjustable length; a sternum strap attached to a front of the shoulder straps and having an adjustable length; and two stretcher carrying loop assemblies connected to a right side of the hip belt and two stretcher carrying loop assemblies connected to a left side of the hip belt.

Other objects, features and advantages of the invention will become apparent from the following detailed description taken in conjunction with the accompanying drawings.

DETAILED DESCRIPTION OF THE PREFERRED EMBODIMENTS

Figure 1:
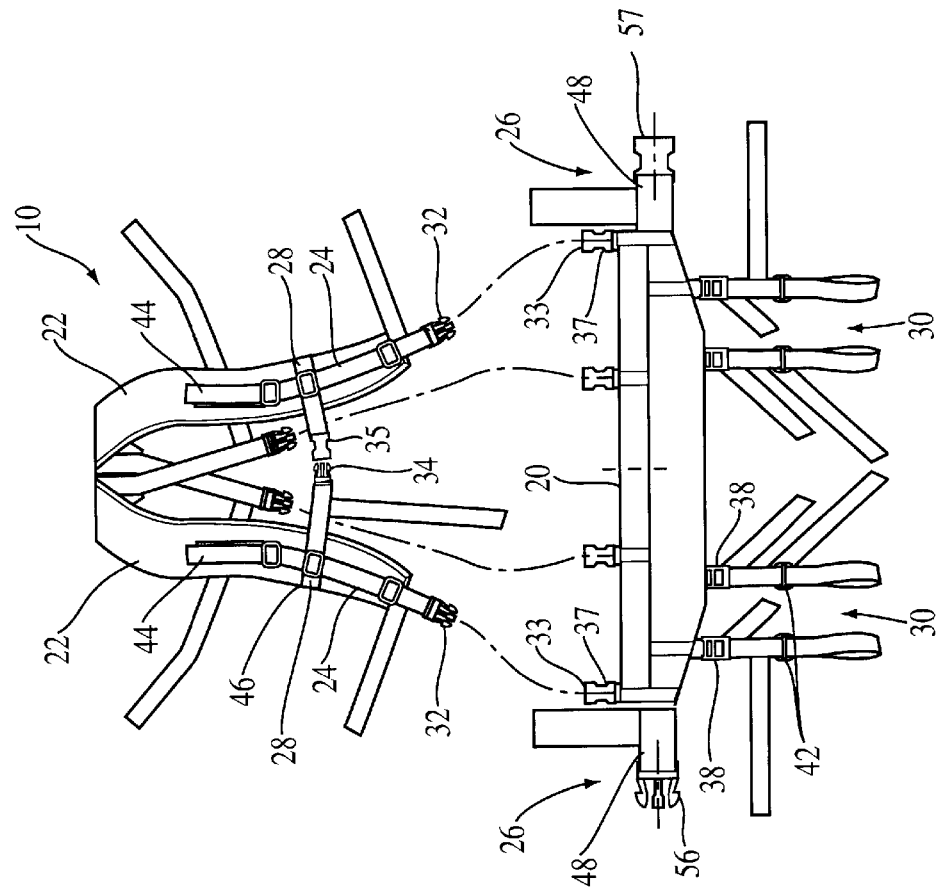
FIG. 1 shows a front view of an embodiment of the harness of the present invention.

In general, the invention is a device which allows th e weight of a stretcher with a casualty to be carried on the shoulders, hips, or hands. The device comprises a harness th at has two padded shoulder straps which are vertically adjustable. The shoulder straps are connected by a horizontal piece of fabric which is horizontally adjustable, bringing the shoulder straps closer together or farther apart. The horizontal strap joining the two shoulder straps allows horizontal adjustment so the load can be displaced to different parts of the shoulder.

The shoulder straps are attached to a padded hip belt. The shoulder straps cross in the back and are sewn together. Buckles on the rear straps allow the harness to b e adjusted to different body sizes. The shoulder straps have tab buckles that allow the load to be shifted from the shoulders to the hips or vice versa. If the large buckle at the hip belt is tightened and the shoulder strap buckles loosened, the load is placed on the hips. The hip belt is horizontally adjustable and covers the back of the waist and the side of the body.

The hip belt includes four fabric loops, two on each side. Webbing is sewn on the hip belt and forms loops on both the right and left side of the hip belt. Stretcher handles are placed in the loops and the loops are vertically adjustable. One stretcher handle goes through both loops on one side. Two loops are needed for stability and the placement of the loops are such that the carrier can grasp the stretcher handles if he or she desires. The two arms of a stretcher are placed in the loops, one arm in two loops. The weight of the stretcher is thus carried on the loops and the harness allows the weight of the stretcher to be transferred to the shoulders, hips or hands.

Throughout the Figures, like reference numerals refer to like features.

Figure 2:
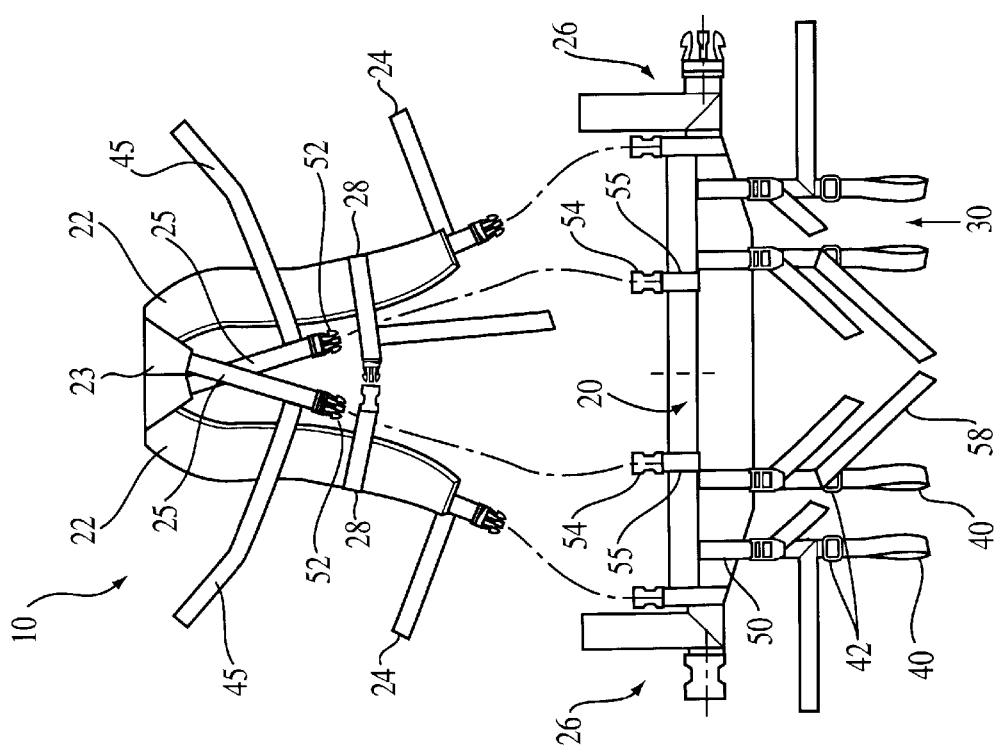
FIG. 2 shows a rear view of the harness of FIG. 1.

FIG. 1 is a front view and FIG. 2 is a rear view of one embodiment of the inventive harness 10. A pair of padded shoulder straps 22 are sewn together with a heavy fabric piece 23 at the rear of the harness. Front and rear shoulder strap adjustment devices 24, 25 are sewn to the shoulder straps 22. The shoulder strap adjustment devices 24 may be made of a 1" nylon fabric strap 44 double stitched to the shoulder straps 22. At the bottom end of each 1" nylon fabric strap 44 is the male portion 32 of a 1" side release buckle. The male portion 32 of the buckle snaps into the female portion 33. The female portion 33 of the buckle is double stitched into 1" nylon fabric 37, which in turn is double stitched into a padded hip belt 20.

The rear shoulder strap adjustment devices 25 are double stitched onto the rear of the shoulder straps 22. The rear shoulder strap adjustment devices 25 may be made of 1 inch wide nylon fabric straps 45, the ends of which contain the male end 52 of a 1" side release buckle. The male portion 52 of the buckle snaps into the female end 54. The female portion 54 of the buckle is double stitched into 1" nylon fabric strap 55, which in turn is double stitched into the hip belt 20.

On the front portion of the shoulder strap 22 is a sternum strap 28. The sternum strap 28 comprises male 34 and female 35 portions of a ¾" side release buckle. The male 34 and female 35 portions of the buckle are attached by ¾" nylon fabric straps 46 to the shoulder straps 22.

The hip belt 20 includes a hip belt adjustment device 26. The hip belt adjustment device 26 comprises a 2" side release buckle, the male 56 and female 57 ends of which are attached to 2" nylon fabric 48. The 2" nylon fabric 48 is secured by double stitching to both ends of the hip belt 20.

Suspended from the hip belt 20 are four stretcher carrying loop assemblies 30. A stretcher carrying loop assembly 30 comprises a superlock holder 38 double stitched to the belt using 1" nylon fabric 50. Suspended from the superlock holder 38 is 1" nylon fabric 58 formed into a loop 40 using a triglide locking collar 42.

Figure 3:
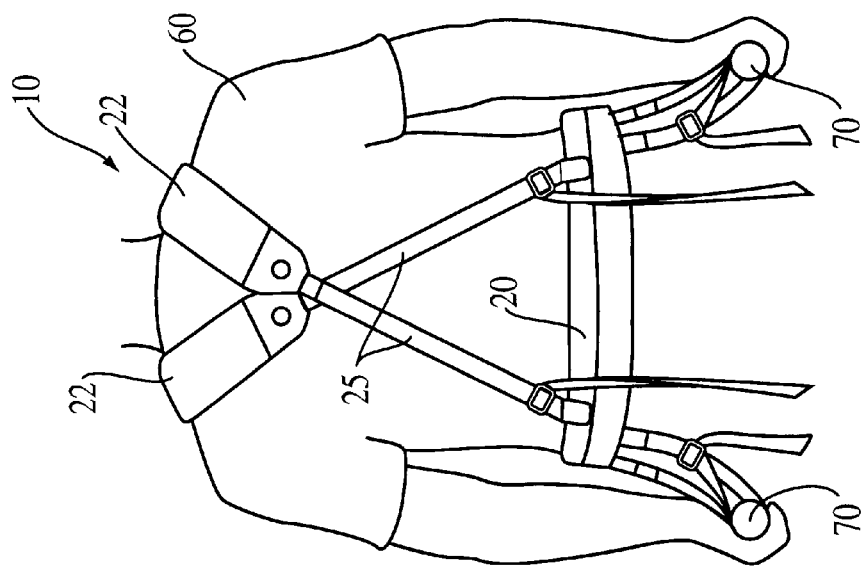
FIG. 3 shows a front view of the inventive harness worn by a person.
Figure 4:
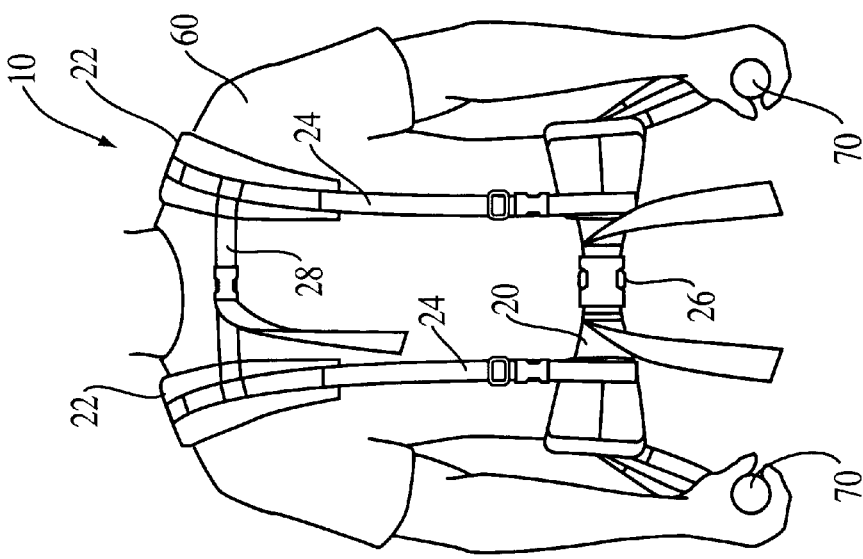
FIG. 4 is a rear view of FIG. 3.

FIGS. 3 and 4 show front and rear views, respectively, of the harness 10 on an individual 60 who is carrying a stretcher with handles 70.

While the invention has been described with reference to certain preferred embodiments, numerous changes, alterations and modifications to the described embodiments are possible without departing from the spirit and scope of the invention as defined in the appended claims, and equivalents thereof.

What is claimed is:

1. A harness for wearing by a person carrying a stretcher, comprising:

a padded hip belt;

a pair of padded shoulder straps joined together at a portion on a rear of the harness;

first and second pairs of shoulder strap adjustment devices disposed on a front and the rear of the harness, respectively, for connecting the pair of shoulder straps to the hip belt, lengths of the first and second pairs of shoulder strap adjustment devices being adjustable;

a hip belt adjustment device having an adjustable length;

a sternum strap attached to a front of the shoulder straps and having an adjustable length; and two stretcher carrying loop assemblies connected to a right side of the hip belt and two stretcher carrying loop assemblies connected to a left side of the hip belt.

2. The harness of claim 1 wherein the second pair of shoulder strap adjustment devices cross over each other and are joined together at a crossover point.

3. The harness of claim 1 wherein the first and second pairs of shoulder strap adjustment devices include side release buckles for connecting to the hip belt.

4. The harness of claim 3 wherein the first and second pairs of shoulder strap adjustment devices each comprise a one inch wide nylon fabric strip.

5. The harness of claim 1 wherein the sternum strap comprises male and female ends of a side release buckle, the ends of the side release buckle being connected to the shoulder straps.

6. The harness of claim 5 wherein the sternum strap comprises a three quarter inch wide nylon fabric strip.

7. The harness of claim 1 wherein the hip belt adjustment device comprises male and female ends of a side release buckle, the ends of the side release buckle being connected to the hip belt.

8. The harness of claim 7 wherein the hip belt adjustment device comprises a two inch wide nylon fabric strip.

9. The harness of claim 1 wherein each of the stretcher carrying loop assemblies comprises a superlock holder connected to the hip belt and a loop suspended from the superlock holder and formed using a triglide locking collar.

10. The harness of claim 9 wherein the superlock holders are connected to the hip belt by one inch wide nylon fabric strips.

11. The harness of claim 10 wherein the loops are comprised of one inch wide nylon fabric strips.

\* \* \* \* \*